United States Patent [19]

Reiter

[11] Patent Number: 4,896,478

[45] Date of Patent: Jan. 30, 1990

[54] METHOD AND APPARATUS FOR STERILIZING PACKAGING MATERIAL, IN PARTICULAR PACKAGING CONTAINERS

[75] Inventor: Michael Reiter, Cologne, Fed. Rep. of Germany

[73] Assignee: PKL Verpackungssysteme GmbH, Duesseldorf, Fed. Rep. of Germany

[21] Appl. No.: 929,949

[22] Filed: Nov. 12, 1986

[30] Foreign Application Priority Data

Nov. 13, 1985 [DE] Fed. Rep. of Germany ....... 3540161

[51] Int. Cl.$^4$ ......................... B65B 55/10; A61L 2/20
[52] U.S. Cl. ........................................ 53/426; 53/141;
261/79.2; 422/28; 422/302; 422/305; 422/306; 141/63
[58] Field of Search .................. 53/426, 141; 422/302, 422/27, 28, 305, 306; 261/79.2, 79.1; 141/63

[56] References Cited

U.S. PATENT DOCUMENTS

| | | | |
|---|---|---|---|
| 4,424,189 | 1/1984 | Hick | 422/27 |
| 4,477,271 | 10/1984 | Iwasyk et al. | 261/79.2 X |
| 4,511,538 | 4/1985 | Buchner et al. | 422/302 X |
| 4,512,935 | 4/1985 | Hilmersson et al. | 422/306 X |
| 4,537,749 | 8/1985 | Hick | 422/302 X |
| 4,631,173 | 12/1986 | Müller et al. | 422/28 |
| 4,742,667 | 5/1988 | Müller et al. | 422/302 X |

Primary Examiner—Horace M. Culver
Attorney, Agent, or Firm—Sprung Horn Kramer & Woods

[57] ABSTRACT

The invention relates to a method and an apparatus for sterilizing packaging material, in particular packaging containers by means of a liquid sterilizing agent containing hydrogen peroxide, in which a mixture consisting of sterilizing agent and air is vaporized within a spray pipe (18) and guided positively within the spray pipe so that a very good vaporization capacity is achieved. In order to achieve this, a rotary flow movement along a central axis is imparted to the mixture of vapor and air by swirl bodies (19, 21) and coil spring inserts (22, 23) inserted alternately therewith inside the spray pipe (18) and the liquid which has not yet vaporized is given a flow direction in opposition to that of the main stream of the mixture and consequently a long residence time of the liquid on the pipe wall of the spray pipe (18) is achieved.

14 Claims, 2 Drawing Sheets

FIG. 2
FIG. 3
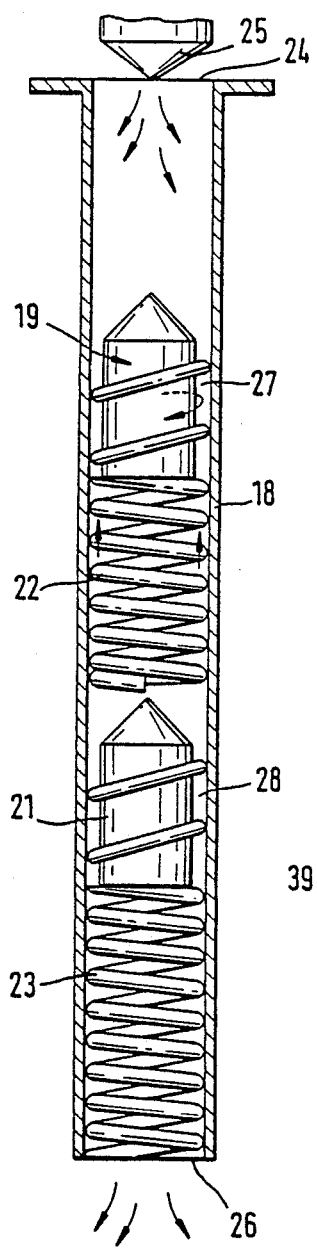
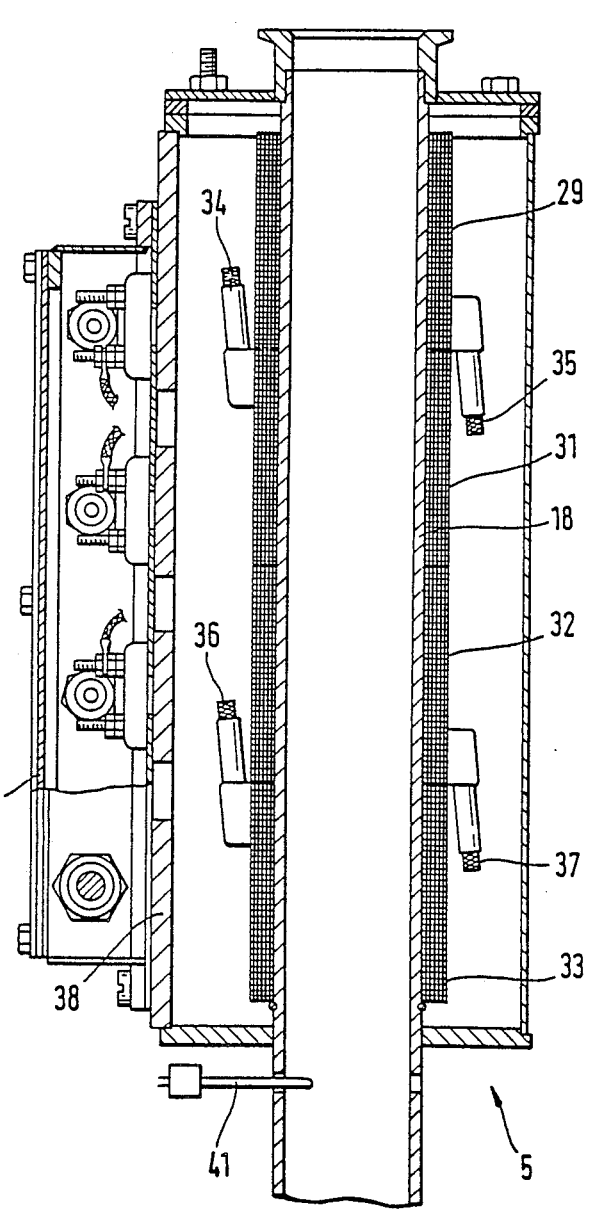

METHOD AND APPARATUS FOR STERILIZING PACKAGING MATERIAL, IN PARTICULAR PACKAGING CONTAINERS

The invention relates to a method for sterilising packaging material, in particular packaging containers, by means of a liquid sterilising agent containing hydrogen peroxide, in which the sterilising agent is atomized and mixed with compressed air, the resulting mixture is vaporized and then the mixture of vapor, air and sterilising agent is set in turbulence and blown onto the surface of the packaging material or packaging container to be sterilised and at this point the vapor is condensed. Furthermore the invention relates to an apparatus for carrying out the method.

In a method according to U.S. Pat. No. 4,631,173 the atomization of the liquid sterilising agent takes place directly by the compressed air, which at the same time is the carrier or conveying agent for the sterilising agent. For example the atomization is carried out by means of a two-component nozzle, so that the necessary mixing with compressed air already takes place at the same time as the fine distribution of the sterilising agent in the form of fine droplets. Due to the fact that the sterilising agent is also atomized over a heated surface, whereof the temperature is considerably higher than the vaporization temperature of the sterilising agent, extraordinarily rapid vaporization of the droplets encountering the surface occurs. The resulting vapor is immediately entrained by the compressed air stream and immediately thereafter reaches the surface of the packaging material or of the packaging container to be sterilised. At this point the vapour condenses. The distribution of the vapor within the air stream eminating from the atomization and the conveyance of the finest droplets which have not yet vaporized is considerably promoted, if vigorous turbulence is produced in the path of the air or vapor-air stream. In the known method this is achieved for example due to the fact that the compressed air stream is directed towards projections, irregularities or the like provided on the heating surface. In a concrete embodiment, these irregularities consist of a coil spring inserted in a spray pipe and guide members attached thereto, which are distributed over the length of the spray pipe at the same distance apart. The guide members constructed as baffle plates are in the shape of a circular surface, from which a circular segment is cut off and starting from the inner wall of the spray pipe, extend at right angles through the cross section of the pipe beyond the longitudinal axis of the spray pipe, so that in the region thereof only part of the free pipe cross section is available as flow cross section.

The known method also operates satisfactorily and there are no noticeable drawbacks. However with an increase in scale of the apparatus, losses in efficiency occur due to heat and material exchange problems. The physical processes which take place in this case should be considered in somewhat more detail hereafter. They are:

1. The transfer of heat from the heat source to the heating surface.
2. The transfer of heat from the heat source to the environment (heat losses).
3. The transfer of heat from the heating surface into the liquid to be heated.
4. The transfer of material of the liquid to the heated surface.

The vaporization capacity is now all the better the more the handicaps for the heat and material transfers listed above under points 1 to 4 can be obviated.

The transfer of heat to the heating surface may be improved by using materials with high coefficients of thermal conductivity, thin wall thicknesses and a construction which favors the flow of heat.

The transfer of heat to the heated wall can be improved by uniform distribution of the liquid on the heating surface, producing high turbulence in the boundary layer of the liquid on the heating surface and finally by increasing the heating surface by profiling or increasing the surface roughness.

The transfer of material of the sterilising liquid to the heated surface represents the greatest problem.

The object of the invention is to propose a method of the aforementioned type, which is characterised by few heat and material exchange problems and thus by a higher vaporization capacity.

This object is achieved according to the invention due to the fact that first of all a rotary movement along a central axis is imparted to the mixture of vapor, air and sterilising agent and then a boundary layer of the mixture liquid produced by the centrifugal action of the rotary flow is guided in a positive manner at least partially in the opposite direction to the main flow movement. The flow of the mixutre of vapor, air and liquid is thus first of all set in rotation, so that the heavier liquid particles pass to the outside due to centrifugal forces and can be heated easily at this point. In this case, the greater the speed of rotation, the better the transfer of heat from the heating surface to the liquid. Furthermore, the liquid must be guided in a positive manner so that the latter does not have the opportunity to flow away in an accumulated manner and without appreciable contact with the heating surface. The positively guided boundary layer of the mixture liquid or parts thereof are in any case held by the rotating main stream at the outside on the heating surface, so that the residence time of the liquid which has not yet vaporized on the heating surface is increased.

In an appropriate embodiment of the method according to the invention, it is provided that the rotating main flow and the oppositely directed positive guidance of the mixture liquid are produced several times in succession. Due to this the above-described effect is considerably improved.

An apparatus which is suitable for carrying out the method comprises within a filling plant for filling material to be introduced into packaging containers, a conveying device for conveying the packaging material or the packaging containers and is provided with a storage container for liquid sterilising agent containing hydrogen peroxide, an atomizer-blower device and a subsequent vaporization device with a spray pipe receiving compressed air, with units constructed as a coil spring and guide member for guiding the flow of the mixture of vapor, air and sterilising agent. In a device of this type, according to the invention the guide member is formed by at least one swirl body inserted in the spray pipe and the coil spring is formed by at least one coil spring insert located behind the swirl body in the spray pipe, seen in the direction of flow and having a pitch extending in the opposite direction to the swirl groove of the swirl body. The swirl body which is kept comparatively short is constructed so that the liquid is forced to flow through the swirl groove and does not have any opportunity to pass downwards along the swirl body in any other way. The swirl body or the swirl groove is preferably right-handed, since a two-component nozzle located above the swirl body for producing a spray cone likewise gives the latter a slight right-hand twist, so that a good flow inlet into the right-handed swirl body is provided. Now the following coil spring insert is provided with an oppositely directed pitch, thus a left-hand pitch. Thus, since the main flow has a right-hand twist, the liquid which accumulates between the wound wire of the coil spring insert, is again driven upwards. If the liquid film forming in this way becomes too great, then the liquid drops down again. However, due to the rotating main flow it will in each case be kept at the outside on the wall of the spray pipe and again passes somewhat deeper into the gaps in the coil spring insert. In this way, the residence time of the non-vaporized liquid on the heated wall of the spray pipe can be considerably increased. The pitch of the coil spring insert has been chosen to be relatively low namely $h = D/8$ (D=diameter of the coil spring), in order that the ascent of the liquid is facilitated. If sufficient liquid is present shortly after the swirl body, then closed liquid bridges form between the coils of the coil spring insert.

It was now found that the afore-described effect can be essentially improved if two swirl bodies and coil spring inserts are located in the spray pipe. In this case it is appropriate if the first swirl body located in the spray pipe is located at a distance from the inlet opening of the spray pipe and the associated coil spring insert is located directly after the swirl body in the spray pipe, whereas the second swirl body located in the spray pipe is seated directly behind the first coil spring insert and the second coil spring insert is seated directly behind the second swirl body in the spray pipe.

The swirl bodies preferably consisting of synthetic material are provided on their side facing the inlet opening of the spray pipe with a conical tip. The inlet into the swirl grooves of the swirl body is thus facilitated.

Finally, better vaporization efficiency can be achieved if the spray pipe can be heated by heating cartridges fitted to its outer diameter and the latter can preferably be monitored individually and controlled electrically. Finally, an insulation of the device has proved advantageous.

Further advantages and features of the present invention will become apparent from the following description of one embodiment with reference to the accompanying drawings and from the other sub claims. In the drawings:

FIG. 2 shows a spray pipe of the vaporizing device equipped with swirl bodies and coil spring inserts and FIG. 3 shows the spray pipe with a heating device.

Figure 1:
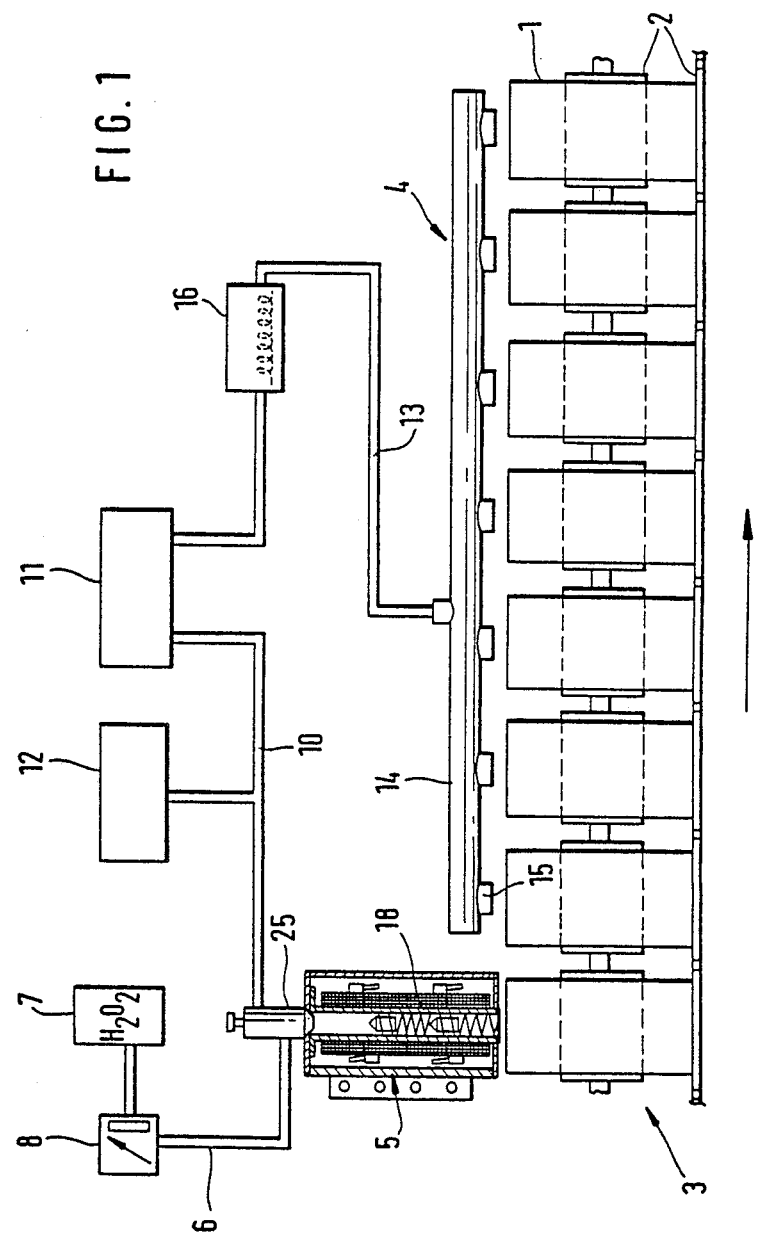
FIG. 1 is a diagrammatic illustration of an apparatus for sterilising packaging containers.

In FIG. 1, a device for sterilising packaging containers 1 is illustrated diagrammatically. This device is part of a filling plant not shown in further detail, in which the packaging containers 1 are first of all made from plastic-coated cardboard blanks, sterilised, filled with a filling material, for example milk, and then sealed. Installations of this type are known and therefore do not need to be described in detail.

Provided for the conveyance of the packaging containers 1 is a conveying device 2 in the form of a bucket chain or the like, in which the packaging containers 1 are held positively and in a stable manner. The conveying device 2 conveys the packaging containers 1 cyclically in the direction of the arrow. At the inlet of the device, the packaging containers pass through a sterilising station 3, which is followed by a drying station 4 consisting of several individual stations each with a station time. A combined atomizer-blowing device 5, which will be described in detail hereafter, is mounted in the sterilising station 3 above the path of movement of the packaging containers 1. The apparatus 5 is connected by way of a pipe 6 to a storage container 7 for a liquid sterilising agent, in this example a 35% aqueous solution of hydrogen peroxide. Inserted in the pipe 6 is a metering device 8 known per se, by which the sterilising agent is supplied to the apparatus 5 in an accurately measured manner. The apparatus 5 is also connected by way of a pipe 10 to a compressed air source 11 shown purely diagrammatically, for example a compressor. The supply of compressed air is monitored and controlled by a control device 12 which is likewise shown solely diagrammatically.

Heated, sterilised air is supplied by way of a pipe 13 to a hot air distributor 14 of the drying station 4. Blowing nozzles 15 project downwards from the hot air distributor 14 and are arranged so that in each individual station of the drying station 4, they are able to blow hot air at a certain temperature (for example 80° C.) and quantity into the packaging containers. The sterile air is taken from an air collecting vessel and heated in a heater 16.

FIG. 2 shows a spray pipe 18 of the combined atomizer-blowing apparatus 5 in vertical longitudinal section, in which case components in the form of two swirl bodies 19, 21 and two coil spring inserts 22, 23 are inserted in the spray pipe 18 and held therein for example by Seeger rings or the like. Located above an inlet opening 24 of the spray pipe 18 is a commercially available two-component atomizer nozzle 25 of the apparatus 5. The spray pipe 18 consisting of a material having good thermal conductivity, for example metal, may be heated in a manner to be described in detail hereafter and to such a degree that the mixture sprayed in a spray mist at the inlet opening 24 by way of the two-component atomizer nozzle 25 is vaporized within the spray pipe 18 and finally can be introduced by way of a lower outlet opening 26 into the packaging container 1 located therebelow.

The spray pipe 18 has a length of 380 mm and at an approximate distance of 75 mm from the upper inlet opening 24 the first swirl body 19 is seated, having a length of approximately 60 mm. Following this is the first coil spring insert 22 having a length of approximately 75 mm and then the second swirl body 21 having a length of 60 mm and finally the second coil spring insert 23 having a length of approximately 110 mm. The swirl bodies preferably consist of synthetic material and have a conical tip in the direction of their inlet side. In the embodiment illustrated, the swirl bodies 19, 21 are right-handed, whereas the coil spring inserts 22, 23 are left-handed. Swirl grooves 27, 28 in the swirl bodies 19, 21 have a height which is approximately four times as great as the spacing of the turns of the coil spring inserts 22, 23, which is approximately 5 mm. The swirl bodies 19, 21 and the coil spring inserts 22, 23 are inserted in a suitable manner in the spray pipe 18, for example they are supported on shoulders or, however in some other manner, for example they are held in the spray pipe 18 by way of Seeger rings or the like. If necessary the swirl bodies 19, 21 and the coil spring inserts 22, 23 may be heated electrically or in some other way.

FIG. 3 shows that the spray pipe 18 can be heated by four heating catridges 29, 31, 32, 33 fitted on its outer diameter and each having a heating capacity of 1.5 kW, whereof the electrical connections are referred to by the reference numerals 34, 35, 36 and 37. The spray pipe 18 with the heating cartridges 29, 31, 32, 33 is located in a housing 38 serving as an insulation, which comprises a junction box 39 for the electrical supply.

Located at the lower end of the spray pipe 18 is a temperature sensor 41, which depending on the temperature of the mixture of vapor and air flowing through the spray pipe 18 controls the supply of heat to the heating cartridges 29, 31, 32, 33 and thus the surface temperature of the inner wall of the spray pipe. The heating cartridges 29, 31, 32, 33 can preferably be monitored individually and controlled electrically. It is thus possible for example that the second and third heating cartridge 31, 32 is supplied with power, because the outlet temperature in the spray pipe has not been reached, but at the same time the fourth heating cartridge 33 does not receive power due to a regulator, because at this point the pre-set maximum temperature of for example 450° C. has been reached. Moreover, depending on the geometry of the components, the various zones of the spray pipe 18 may reach different temperatures. There is therefore a direct connection between the segmental heating of the spray pipe 18 and the components of varying geometry. In the case of higher quantities, it is possible to operate with three stages for example, due to which other temperatures are required at the four segments of the spray pipe. Where swirl bodies are located, there is less fluid and thus a lower temperature is required, for example 250° C. instead of 450° C. normally.

The apparatus according to the invention operates as follows:

The mixture consisting of sterilising agent and air is blown by way of a two-component atomizer nozzle 25 in a spray cone downwards into the spray pipe 18. Since the two-component atomizer 25 gives the spray cone a slight right-hand twist, in conjunction with the conical tip of the upper swirl body 19, the latter passes unhindered into the right-handed swirl groove 27 of the swirl body 19, so that the stream of air and liquid is set in rotation, due to which the heavier liquid particles pass by centrifugal forces towards the outside onto the heated wall of the spray pipe 18. The greater the speed of rotation, the better the transfer of heat from the heated wall of the spray pipe 18 to the liquid.

After leaving the comparatively short swirl body 19, the rotating mixture of vapor, water and air arrives in the region of the first coil spring insert 22. Since the main stream has a right-hand twist and the coil spring insert 22 is left-handed, the liquid which has accumulated between the wound spring wire, is again driven upwards. If the film of liquid forming becomes too great, the liquid again drops down. However, in this case it is always held on the outside against the inner wall of the spray pipe 18 by the rotating main flow and passes again somewhat deeper into the gaps of the coil spring insert. This effect is repeated by the following swirl body 21 and the second coil spring insert 23, so that in total the residence time of the liquid on the wall of the spray pipe 18 is appreciably increased and thus the complete vaporization of the liquid mixture is considerably promoted.

With an apparatus according to the invention one achieves a vaporizer heating with which a mass flow of m>0.8 g/sec. 35% $H_2O_2$ can be vaporized and super heated to a temperature of T>150° C. Experiments have shown that only approximately 6% of the electrical energy supplied is radiated as heat losses. The developed vaporizer heating accordingly works with an efficiency of 94%. At maximum load the consumption is approximately 3 kWH/hour.

It will be understood that the specification and examples are illustrative but not limitative of the present invention and that other embodiments within the spirit and scope of the invention will suggest themselves to those skilled in the art.

What is claimed:

1. In the sterilising of packaging material such as packaging containers by means of a liquid sterilising agent, comprising atomizing the sterilising agent and mixing it with compressed air, vaporizing the resulting mixture, and blowing the mixture of vapor, air and sterilising agent onto the surface of the packing material, the vapor condensing on the packaging material, the improvement which comprises imparting to the mixture, prior to blowing onto the packaging material, a rotary movement along a central axis, and then positively guiding a boundary layer of the mixture liquid produced by the centrifugal action of the rotary flow at least partially in the opposite direction to the main flow direction of the mixture.

2. The method according to claim 1, wherein rotary movement of the main flow and the positive guidance of the boundary layer of the mixture liquid directed in opposition to the main flow are effected several times in succession.

3. In a filling plant for filling material to be introduced into packaging containers, including a conveying device for conveying packaging containers, a supply container for liquid sterilising agent, an atomization-blowing device, a subsequent vaporizing device with a spray pipe supplied with compressed air, and units constructed as a coil spring and a guide member for guiding the flow of the mixture of vapor, air and sterilising agent, the improvement wherein the guide member is formed by at least one swirl body inserted in the spray pipe and having a swirl groove, the coil spring including at least one coil spring insert located behind the swirl body in the spray pipe and having a pitch extending in the opposite direction to the swirl groove of the swirl body.

4. An apparatus according to claim 3, wherein two swirl bodies and coil spring inserts are located alternately in the spray pipe.

5. An apparatus according to claim 3, wherein the swirl groove of the swirl body is right-handed and the pitch of the coil spring insert is left-handed.

6. An apparatus according to claim 3, wherein the swirl body located at the inlet side in the spray pipe is arranged at a distance from the inlet of the spray pipe and the associated coil spring insert is located directly adjoining the swirl body in the spray pipe.

7. An apparatus according to claim 4, wherein the swirl body located at the outlet side in the spray pipe is located substantially immediately behind the first coil spring insert and the latter is located immediately behind the second swirl body in the spray pipe.

8. An apparatus according to claim 3, wherein the swirl body is formed of synthetic material and comprises a conical tip on its side facing the inlet of the spray pipe.

9. An apparatus according to claim 3, wherein when more than one swirl body is present all have substantially the same length and each is shorter than its coil spring insert.

10. An apparatus according to claim 4, wherein the coil spring insert facing the outlet of the spray pipe terminates flush with the latter and is longer than the first coil spring insert.

11. An apparatus according to claim 3, wherein the pitch height of the swirl grooves of a swirl body is approximately four times as great as the pitch height of the turns of its coil spring insert.

12. An apparatus according to claim 3, including heating cartridges fitted on the outside of the spray pipe.

13. An apparatus according to claim 12, including means for electrically operating and individually monitoring the heating cartridges.

14. An apparatus according to claim 12, including insulation surrounding the heating cartridges.

* * * * *